United States Patent [19]

Metala et al.

[11] Patent Number: 4,856,337
[45] Date of Patent: Aug. 15, 1989

[54] APPARATUS AND METHOD FOR PROVIDING A COMBINED ULTRASONIC AND EDDY CURRENT INSPECTION OF A TUBE

[75] Inventors: Michael J. Metala; William G. Clark, Jr., both of Murrysville; Warren R. Junker, Monroeville; Lee W. Burtner, Elizabeth Twp., Allegheny County; Thomas E. Arzenti, Greensburg; Harold P. Johnson, Verona; Robert P. Vestovich, Monroeville; Bruce W. Bevilacqua, Irwin, all of Pa.

[73] Assignee: Westinghouse Electric Corp., Pittsburgh, Pa.

[21] Appl. No.: 79,860

[22] Filed: Jul. 30, 1987

[51] Int. Cl.$^4$ ............................................. G01N 29/00
[52] U.S. Cl. .................................... 73/601; 73/623; 324/226
[58] Field of Search ............... 376/252, 249; 324/226; 73/601, 622, 623, 633, 634

[56] References Cited

U.S. PATENT DOCUMENTS

| | | | |
|---|---|---|---|
| 3,238,448 | 3/1986 | Wood et al. | 324/37 |
| 3,810,384 | 5/1974 | Evans | 73/623 |
| 3,817,089 | 6/1974 | Eggleton et al. | 73/67.85 |
| 3,845,463 | 10/1974 | Timbs | 340/5 R |
| 4,008,603 | 2/1977 | Paulissen | 73/67.85 |
| 4,096,757 | 6/1978 | Ishii et al. | 73/621 |
| 4,167,878 | 9/1979 | Bottcher et al. | 73/601 |
| 4,189,944 | 2/1980 | Day et al. | 73/623 |
| 4,361,044 | 11/1982 | Kupperman et al. | 73/623 |
| 4,388,831 | 6/1983 | Sherman | 73/623 |
| 4,418,574 | 12/1983 | Fluornoy | 73/601 |
| 4,438,399 | 3/1984 | Schnabl et al. | 324/220 |
| 4,452,753 | 6/1984 | Wentzell et al. | 376/260 |
| 4,523,470 | 6/1985 | Muller et al. | 73/623 |
| 4,572,201 | 2/1986 | Kondo et al. | 128/660 |
| 4,597,294 | 7/1986 | Brill, III et al. | 73/623 |
| 4,602,212 | 7/1987 | Hiroshima et al. | 324/227 |
| 4,642,215 | 2/1987 | Klinvex et al. | 376/249 |

FOREIGN PATENT DOCUMENTS 56-154657 11/1981 Japan .
252631 9/1987 U.S.S.R. .

OTHER PUBLICATIONS

Article Appearing in "Nuclear Plant Safety", Nov.–Dec. 1986 Entitled "NDE Technology Development for Steam Generator Tubing Inspection" by Todd A. Richards and S. W. Glass, The Babcock & Wilcox Company.

Primary Examiner—Stewart J. Levy
Assistant Examiner—Louis M. Arana

[57] ABSTRACT

Both an apparatus and a method for simultaneously inspecting the walls of a tube with both ultrasonic and eddy current probes is disclosed herein. The apparatus generally comprises a cylindrical housing assembly insertable within the tube to be inspected, and a probe carrier rotatably mounted within and helically movable with respect to the housing. The probe carrier holds three ultrasonic probes for transmitting ultrasonic beams which are directly oriented radially, chordally, an axially with respect to the longitudinal axis of the tube, as well as an eddy current probe for simultaneously inspecting the walls of the tube with electromagnetic lines of flux. The apparatus further includes a helical drive train formed from a lead screw assembly having a motor means, a drive shaft, and a drive sleeve for imparting a helical scanning motion to the probe carrier with respect to the housing. The interior of the drive sleeve is slidably engaged to the shaft which is in turn coupled to the output of the motor, while the outside of the drive sleeve is threadedly engaged to the interior of the housing. The probe carrier is in turn coupled to the drive sleeve. In the method of the invention, the data generated by the three eddy current probes is correlated with the data generated by the eddy current probe for each specific section of the tube, and displayed simultaneously to the system operator. The resulting complementary display of both ultrasonic and eddy current probe information allows the system operator to accurately determine the size, shape and nature of any flaws which may be present in the walls of the tube.

31 Claims, 4 Drawing Sheets

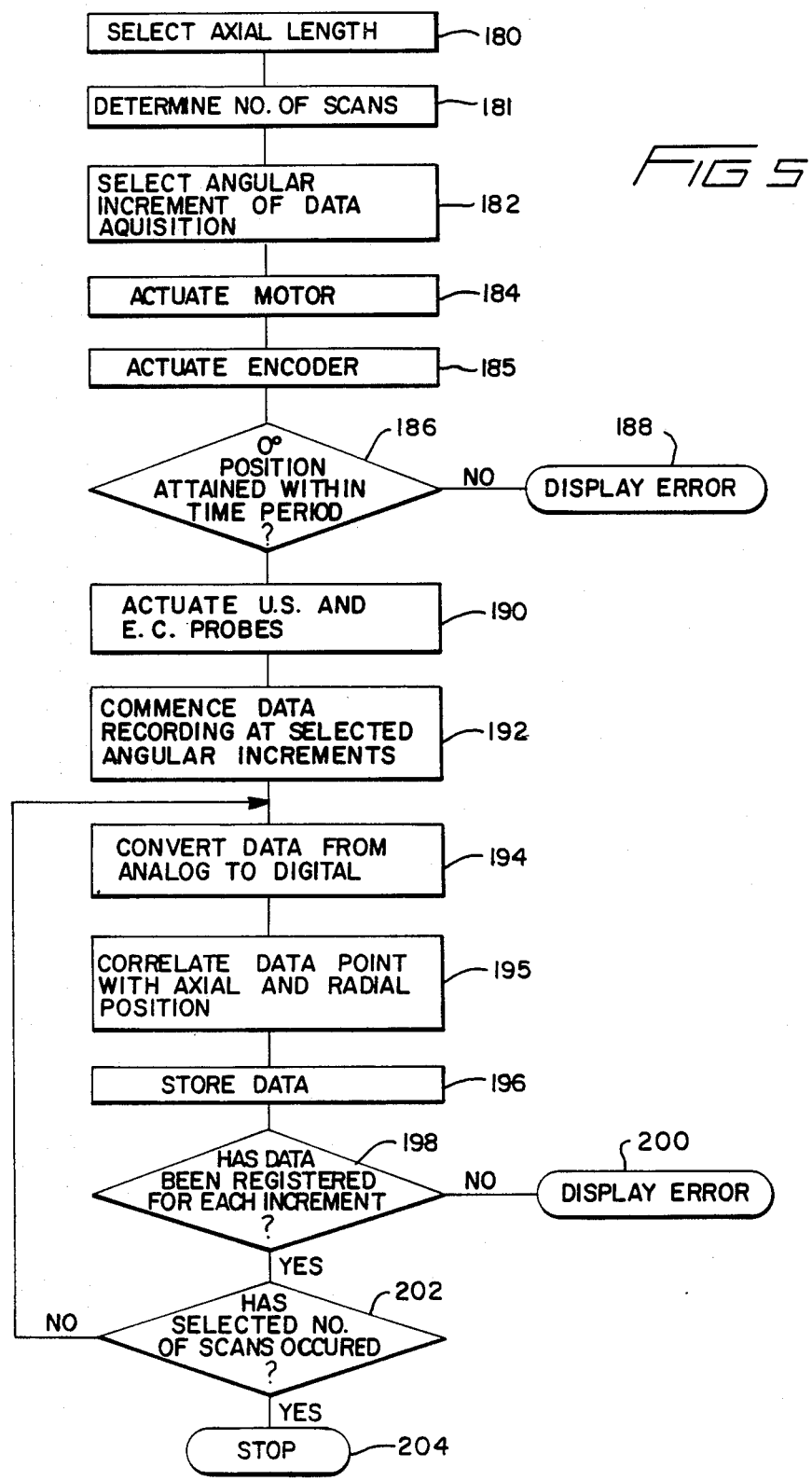

APPARATUS AND METHOD FOR PROVIDING A COMBINED ULTRASONIC AND EDDY CURRENT INSPECTION OF A TUBE

BACKGROUND OF THE INVENTION

This invention generally relates to devices and methods for inspecting conduits, and is specifically concerned with an apparatus and a method for simultaneously inspecting the walls of heat exchanger tubes in nuclear steam generators with both ultrasonic and eddy current probes.

Devices for inspecting the walls of conduits such as the heat exchanger tubes of a steam generator are known in the prior art. Generally, such devices have included either ultrasonic probes, or eddy current probes to inspect the walls of tubes for flaws, but not both. However, before the purpose and operation of such inspecting devices may be fully appreciated, some knowledge of the structure, operation and corrosion degradation problems associated with the heat exchanger tubes in steam generators is necessary.

Nuclear steam generators are comprised of three principal parts, including a secondary side, a tube sheet, and a primary side which circulates water heated from a nuclear reactor. The secondary side of the generator includes a plurality of U-shaped heat exchanger tubes, as well as an inlet for admitting a flow of water. The inlet and outlet ends of the U-shaped tubes within the secondary side of the generator are mounted in the tubesheet which hydraulically isolates the primary side of the generator from the secondary side. The primary side in turn includes a divider sheet which hydraulically isolates the inlet ends of the U-shaped tubes from the outlet ends. Hot water flowing from the nuclear reactor is admitted into the section of the primary side containing all of the inlet ends of the U-shaped tubes. This hot water flows through these inlets, up through the tubesheet, and circulates around the U-shaped tubes which extend within the secondary side of the generator. This water from the reactor transfers its heat through the walls of the U-shaped heat exchanger tubes to the nonradioactive feedwater flowing through the secondary side of the generator, thereby converting feedwater to nonradioactive steam which in turn powers the turbines of an electric generator. After the water from the reactor circulates through the U-shaped tubes, it flows back through the tubesheet, through the outlets of the U-shaped tubes, and into the outlet section of the primary side, where it is recirculated back to the nuclear reactor.

Over a period of time, sludge consisting of magnetite other potentially corrosive chemicals may accumulate in the annular spaces between the heat exchanger tubes and the tubesheet and support plates which surround them. Despite the fact that the heat exchanger tubes are formed from a corrosion-resistant alloy such as Inconel ®, these corrosive chemicals, in combination with the hot water which flows around such tubes, may cause a number of different forms of corrosion degradation, one of which is intra-granular stress corrosion cracking. If unchecked, such corrosion may ultimately result in fissures in the walls of the tubes, which can cause water leakage through the walls of these tubes. In addition to reducing the efficiency of the steam generator as a whole, such leakage may cause radioactive elements carried by the water from the primary side of the generator to contaminate the nonradioactive water in the secondary side, thereby rendering the steam created by the generator undesirably radioactive.

In order to prevent such corrosion degradation from creating leaks in the heat exchanger tubes, a number of maintenance procedures have been developed, one of the most common of which is the installation of reinforcing sleeves on the inner walls of the tubes across the corrosion-degraded portions. This process is called "sleeving". In the case of badly corroded tubes, another type of maintenance procedure has been developed which involves the plugging of the inlet end of the tube. While the plugging of a tube solves the most critical problem of radioactive water from the primary side leaking into the nonradioactive water of the secondary side, it is, of course, less desirable since it lessens the overall heat-exchange capability of the secondary side of the generator.

In order to repair tubes at the earliest possible states of corrosion and to thereby avoid the necessity of plugging tubes, both ultrasonic probes and eddy current probes have been used to inspect the interior walls of such heat exchanger tubes for degradation which indicates the beginning of a corrosive pattern. In inspection devices utilizing ultrasonic probes, several transducer may be oriented both radially and transversely with respect to the longitudinal axis of the tube or pipe being inspected so that cracks of virtually any orientation in the walls of the tube or pipe may be detected. In inspection devices utilizing eddy current probes, a single coil whose axis of rotation is concentric with the axis of rotation of the tube or pipe itself may be used to determine the axial position of a flawed portion of tube wall.

Unfortunately, each type of prior art inspection device is limited in its ability to perfectly inform the operator of the size, shape and type of a corrosion-induced flaw in a small-diameter tube such as the Inconel ® tubes used in nuclear steam generators. For example, some prior art ultrasonic inspection devices utilize a radial array of multiple ultrasonic transducers to broadcast a radial array of ultrasonic beams completely around the circumference of a tube or a pipe. But such configurations are not adaptable for use in small-diameter tubes in view of the relatively large minimum diameter that such devices must have in order to provide a circular arrangement of ultrasonic transducers. To achieve a more compact design, other ultrasonic inspection devices have been developed wherein the ultrasonic transducers are located on the ends of the probe and direct beams of ultrasound along the longitudinal axis of the device into a rotating ultrasonic mirror which is tilted 45° with respect to the probe axis. However, the use of such mirrors creates echoes of ultrasound which in turn generates spurious modes that undermine the accuracy of the device. While eddy current probes are known which are small enough to easily fit within a small-diameter heat exchanger tube, they suffer from other limitations, the most notable being an inability to detect shallow cracks across the thickness of the tube wall. Such probes are also relatively blind to regions where the entire wall has been thinned by a uniform, nonlocalized attack of corrosion.

Clearly, there is a need for a tube inspecting device which is small enough to be used in the heat exchanger tubes of a nuclear steam generator, but yet which is capable of detecting flaws in the walls of these tubes with greater accuracy and reliability than the prior art. Ideally, such an inspection device would be capable of resolving all types of flaws, regardless of shape or orientation, as well as areas where the walls have been uniformly thinned by corrosion or by fretting. Finally, such a device should be reliable in operation, and relatively easy to manufacture from commercially available components.

SUMMARY OF THE INVENTION

Generally speaking, the invention is an apparatus for ultrasonically and electromagnetically inspecting the walls of a conduit, which may be a heat exchanger tube in a nuclear steam generator. The inspection apparatus comprises a housing assembly that is insertable within the tube, and a probe carrier which is rotatably mounted onto this housing assembly. The probe carrier includes three ultrasonic probes for transmitting ultrasonic beams radially, chordally and axially with respect to the longitudinal axis of the tube. To avoid the creation of echoes which can produce spurious modes of ultrasound, each of the ultrasonic probes transmits its respective beam of sound directly at the wall of the tube without the use of ultrasound mirrors. The probe carrier also includes an eddy current probe for simultaneously inspecting the metallic walls of the tube with an electromagnetic field while the probe carrier is rotated.

The inspection apparatus may further include a helical drive train having a lead screw assembly for axially and rotatably moving the probe carrier with respect to the tube. This helical drive train preferably includes a motor means for rotating the probe carrier with respect to the housing, as well as a relatively drag-free optical encoder means for monitoring the number of times the probe carrier is rotated with respect to the housing assembly. The lead screw assembly may include a drive shaft that is slidably connected to a drive sleeve for coupling the output of the motor means with the probe carrier. The exterior of the drive sleeve may be threadedly engaged to the interior of the housing assembly, so that the drive sleeve moves in screw-wise fashion when rotated by the drive shaft. The shaft may have a centrally disposed bore for housing wires which connect the ultrasonic probes to a source of power. Additionally, the housing assembly may contain a slip ring for conducting electricity from these wires to the ultrasonic probes rotating on the probe carrier.

The use of a lead screw assembly in the drive train advantageously necessitates only one optical encoder, since the axial distance of travel may be inferred from the screw pitch and the number of rotations indicated by the encoder.

In the preferred embodiment, the motor means, the drive shaft, and the drive sleeve are all arranged colinearly so as to minimize the overall width of the apparatus. Additionally, the pitch of the threads of the drive sleeve is preferably about 1/28 inches so as to provide a relatively fine scanning resolution on the part of the probe carrier.

The method of the invention generally includes the steps of inserting the inspection apparatus within a conduit such as the heat exchanger tube of a steam generator, helically moving the probe carrier in screw-wise fashion with respect to the tube in order to simultaneously scan the walls of the tube with both ultrasonic and eddy current probes, correlating the resulting ultrasonic and eddy current scan data for each axial and radial point of the tube, and then displaying this data for each axial and radial coordinate of the tube being inspected. The correlation of both the ultrasonic and the eddy current probe data for each radial and axial point along the walls of the tube being inspected provides the operator with complementary information concerning the type, shape, and characteristics of any flaws which may exist in the tube wall.

BRIEF DESCRIPTION OF THE SEVERAL FIGURES

Figure 4A:
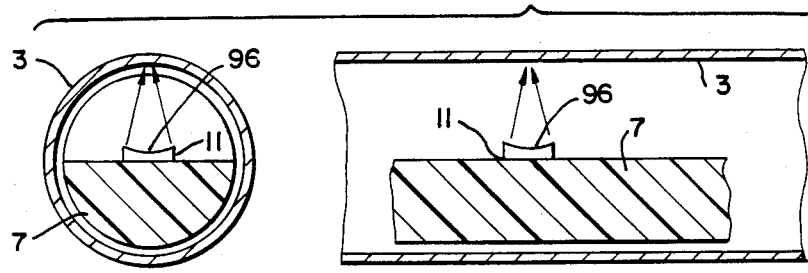
Figure 4B:
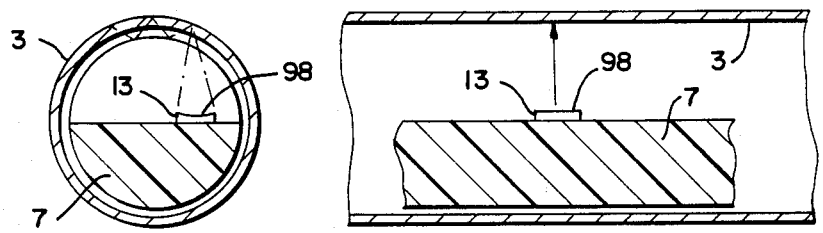
Figure 4C:
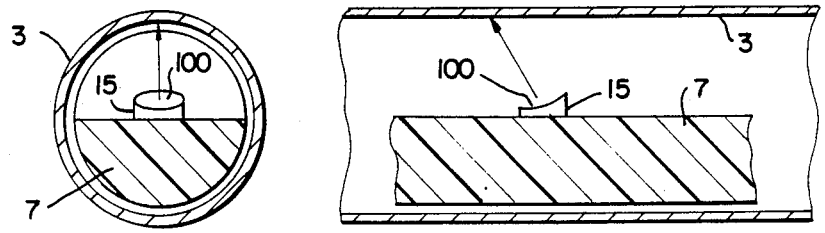

FIGS. 4A, 4B and 4C each illustrate the orientation of the ultrasonic beam emitted by each of the three ultrasonic probes mounted on the probe carrier, respectively, and FIG. 5 is flowchart illustrating the method of the invention.

DETAILED DESCRIPTION OF THE PREFERRED EMBODIMENT

General Overview of the Structure and Operation of the Invention

Figure 1:
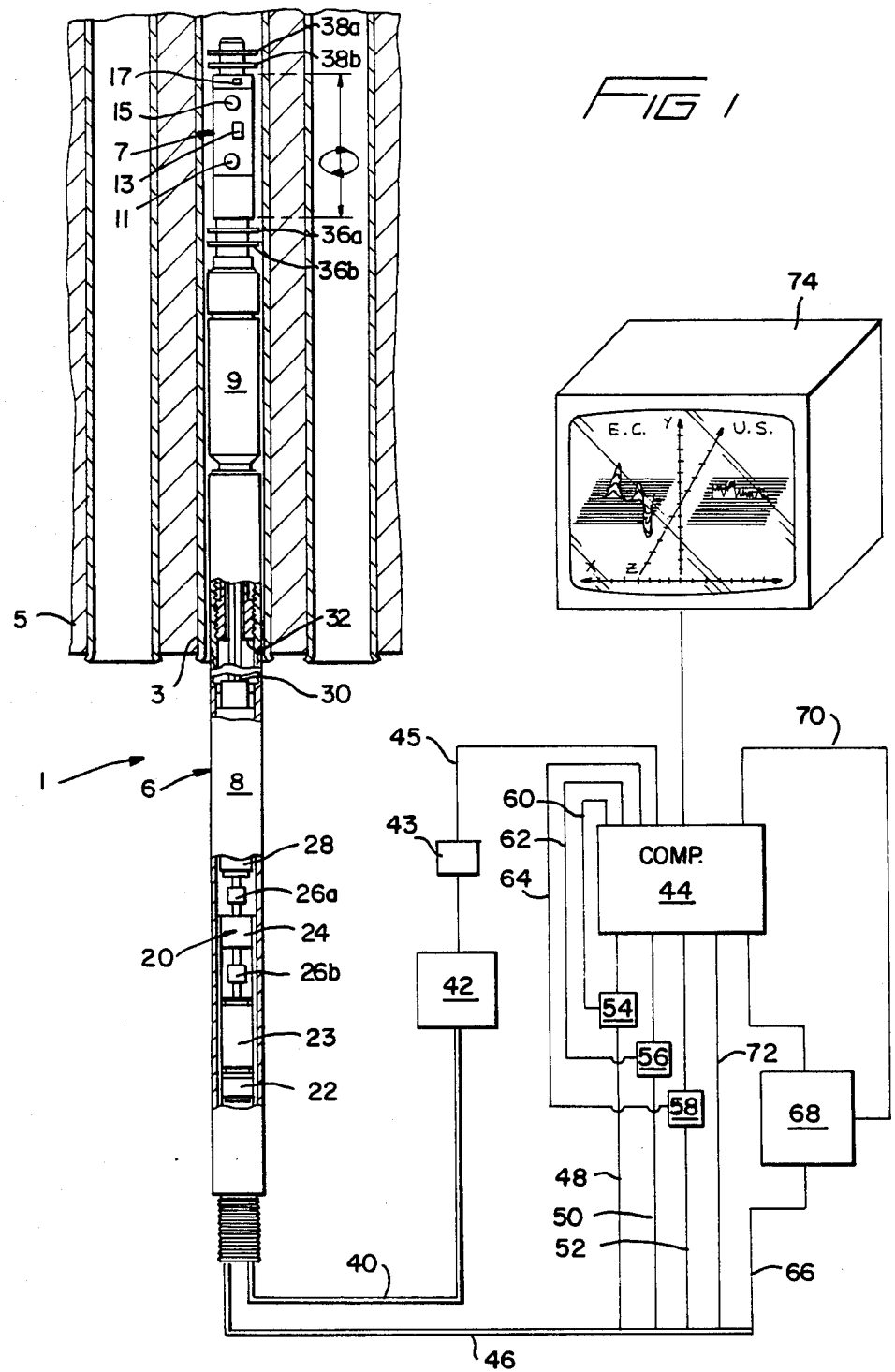
FIG. 1 is a schematic and partial, cross-sectional side view of the combined ultrasonic and eddy current inspection apparatus of the invention.

With reference to FIG. 1, wherein like numerals designate like components throughout all the several figures, the inspection apparatus 1 of the invention is particularly adapted for providing an ultrasonic and eddy current scan of the walls of a selected heat exchanger tube 3 mounted in the tubesheet 5 of a nuclear steam generator (not shown). The inspection apparatus 1 generally comprises a housing assembly 6, and a probe carrier 7 which carries three ultrasonic probes 11, 13 and 15, as well as an eddy current probe 17. The proximal end of the housing assembly 6 includes a drive train housing 8, which remains stationary during the operation of the inspection apparatus 1. The distal end of this assembly 6 includes a cable housing 9 which rotates and advances or retracts axially with respect to the drive train housing 8 during the operation of the apparatus 1. The cable housing 9 is in turn connected to the probe carrier 7, and serves to move it along a helical path. As may best be seen with respect to FIGS. 3 and 4A, 4C, the probe carrier 7 includes, in its central portion, the three ultrasonic probes 11, 13 and 15 which direct ultrasonic beams radially, chordally and axially, respectively. Additionally, the distal annular shoulder of the probe carrier 7 carries the eddy current probe 17. As may best be seen in FIG. 1, the helical, screw-type motion of the probe carrier 7 relative to the drive train housing 8 results in a helical scanning of an axial section of a heat exchanger tube 3, first by an eddy current probe 17, then by the axially, chordally and radially oriented probes 15, 13 and 11, respectively.

The drive train housing 8 of the housing assembly 6 contains a helical drive train 20 which is responsible for imparting the helical or screw-wise motion to the cable housing 9 and the probe carrier 7 connected thereto. The helical drive train 20 is formed from a co-linear arrangement of an electric motor 22, a gearbox 23, and an optical encoder 24. Shaft couplings 26a and 26b connect the input shaft of the optical encoder 24 to the output shaft of the gearbox 23, and the output shaft of the encoder 24 to the input shaft of a slip ring 28. As will be discussed in more detail hereinafter, the slip ring 28 allows the ultrasonic and eddy current probes 11, 13, 15 and 17 to be connected to their various power sources despite the relative rotary movement between these probes on the probe carrier 7, and the stationary drive train housing 8. The combination of rotary and axial movement imparted to the probe carrier 7 is accomplished by a lead screw assembly 29 formed from a drive shaft 30 of hexagonal cross section and a drive sleeve 32 that is integrally connected to the rotatably movable cable housing 9. The hexagonal shaft is slidably movable within a hexagonal bore centrally disposed within the drive sleeve 32. The exterior of the drive sleeve 32 includes screw threads which are engaged to complementary screw threads in the interior walls of the proximal end of the drive train housing 8. Hence, when the hexagonal shaft 30 is rotated, both the cable housing 9 and the probe carrier 7 are helically moved in screw-wise fashion in an axial direction which depends upon whether the shaft of the motor 22 is driven clockwise, or counterclockwise. Proximal centering disks 36a, 36b and distal centering disks 38a, 38b are provided on the proximal and distal ends of the probe carrier 7 to help maintain the annular shoulders on either side of the probe carrier 7 in concentric alignment with the axis of rotation of the tube 3.

FIG. 1 also illustrates the components which control the actuation of and rotational direction of the motor 22 of the helical drive train 20, as well as the actuation and de-actuation of the various probes mounted on the probe carrier 7. A cable 40 connects the motor 22 to a power source 42. Both the actuation of the power source 42 and the polarity of the DC current admitted through cable 40 is in turn controlled by a switching circuit 43. The switching circuit 43 is in turn controlled by and connected to a computer processing unit 44 via output lead 45. In the preferred embodiment, the computer 44 is a model no. LSI 11/23 computer manufactured by the Digital Equipment Corporation located in Waltham, Mass. However, any current model of an IBM personal computer may also be used.

The ultrasonic probes 11, 13 and 15 are each ultimately connected to an individual ultrasonic pulser-receiver by way of cable 46. Specifically, the radial beam probe 11, the chordal beam probe 13, and the axial beam probe 15 are connected by individual leadwires 48, 50 and 52 to their own individual ultrasonic pulser-receivers 54, 56 and 58, respectively. In the preferred embodiment, each of the ultrasonic pulser-receivers is a Sonic Mark II manufactured by Sonic Instruments Company, Inc., located in Trenton, New Jersey. The outputs of each of these ultrasonic pulser-receivers 54, 56 and 58 is connected into the input side of the computer 44 as shown, while the input of each of these ultrasonic pulser-receivers is connected to an output lead 60, 62 and 64 of the computer 44 so that the computer 44 may actuate or de-actuate each of the pulser-receivers. The eddy current probe 17 is connected by way of cable 46 and individual lead wire 66 to the input end of a multiple-frequency eddy current tester 68 as shown. In the preferred embodiment, eddy current tester 68 is preferably a MIZ-12 model tester manufactured by Zetec, Inc., located in Isaquah, Wash. The output of the eddy current tester 68 is connected to the input of the computer 44 as shown, while the input of this tester 68 is connected to the output of the computer 44 via output lead wire 70. Finally, the output of the optical encoder 24 is connected to the input side of the computer 44 via cable 46 and lead wire 72.

As will be discussed in more detail hereinafter, the computer 44 includes a buffer memory storage for recording the data generated by each of the ultrasonic and eddy current probes 11, 13, 15 and 17 for each helical scan made around the tube 3. The computer 44 is programmed to correlate each of the ultrasonic and eddy current data points with a particular axial and radial coordinate an to simultaneously display them on a cathode ray tube 74, where the Z axis corresponds to points along the longitudinal axis of the tube 3, and the X axis corresponds to a specific radial position around the interior wall of the tube as measured by the optical encoder 24.

Specific Description of the Structure, Operation and Method of the Invention

Figure 2:
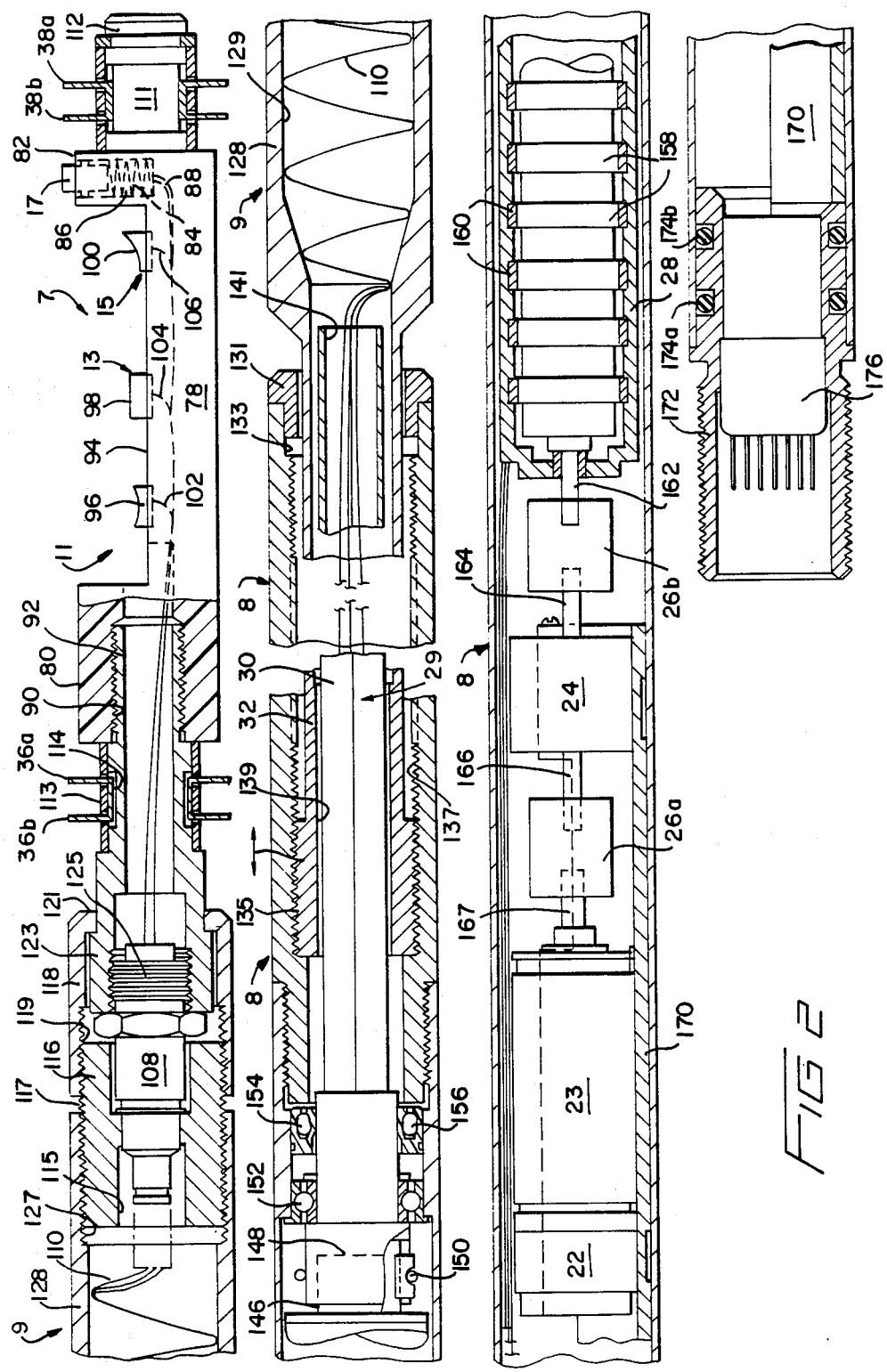
FIG. 2 is an enlarged cross-sectional side view of the cylindrical housing assembly and probe carrier of the apparatus illustrated in FIG. 1.
Figure 3:
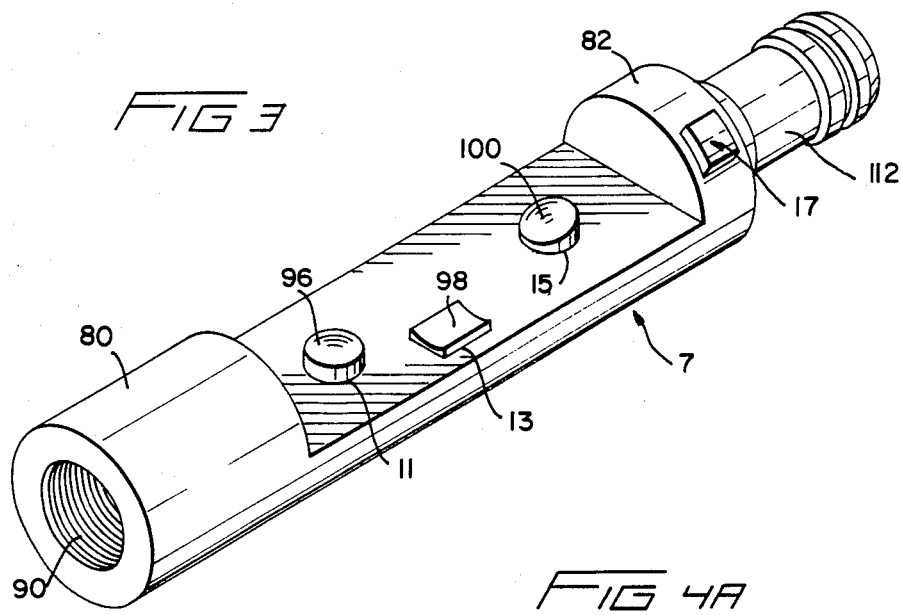
FIG. 3 is a perspective view of the probe carrier of the apparatus showing the relative positions of the three ultrasonic probes and one eddy current probe mounted thereon.

With reference now to FIGS. 2 and 3, the probe carrier 7 of the apparatus 1 has a semi-cylindrical body 78 which is preferably formed from a highly dielectric material which is easily molded, such as Delrin ®. This semi-cylindrical body 78 has proximal and distal annular shoulders 80 and 82 which are complementary in function to the proximal and distal centering disks 36a, 36b and 38a, 38b which help keep the semi-cylindrical body 78 concentrically aligned within the heat exchanger tube 3 being inspected. The distal annular shoulder 82 includes a radially disposed bore 84 for housing the previously mentioned eddy current probe 17. In the preferred embodiment, the eddy current probe 17 is a pancake-type probe encapsulated in nylon or some other self-lubricating plastic material. A coil spring 86 housed within the radial bore 84 resiliently biases the eddy current probe 17 outwardly, so that the top surface of the probe 17 floatingly engages the interior walls of the tube 3 being inspected when the probe carrier 7 is rotated. A stop ledge (not shown) circumscribes the eddy current probe 17 and co-acts with a circumferential lip (also not shown) within the bore 84 in order to limit the radial extent to which the eddy current probe 17 may extend out of shoulder 80. The eddy current probe 17 includes lead wires 88 embedded in the semi-cylindrical body 7 8 which ultimately connected to the previously mentioned central processing unit 44. In operation, the use of a self lubricating plastic to encase the eddy current probe 17 advantageously minimizes the frictional drag between the probe 17 and the interior wall of the tube 3 while protecting the delicate coil windings. Additionally, the floating engagement afforded by the radial biasing of the probe 17 by the coil spring 86 maintains the windings of the end current probe 17 a uniform radial distance away from the walls of the tube 3 despite any deviations in the generally circular cross section which characterizes such tubes 3. Finally, the use of a moldable, dielectric material for the fabrication of the probe carrier 7 minimizes inaccuracies that could result from spurious electromagnetic coupling between the probe body 7 and the eddy current coil 17.

The proximal annular shoulder 80 of the semicylindrical body 78 includes a threaded axial bore 90. This bore 90 receives the threads of a nipple member 92 which connects the body 78 to the previously mentioned cable housing 9 of the housing assembly 6. The flat side of the centrally located, semi-cylindrical portion of the body 78 includes a mounting surface 94 on which the radial beam ultrasonic probe 11, chordal beam ultrasonic probe 13, and axial beam ultrasonic probe 15 are mounted. Each of the probes 11, 13 and 15 includes a piezo-electric transducer for converting an alternating current into ultrasonic energy, as well as its own beam-directing reflector 96, 98 and 100, respectively. The beam-directing reflector 96 of ultrasonic probe 11 has a concave, spherical contour and is located over the axis of rotation of the probe carrier 7 in order to focus a point-like, radially directed beam of ultrasound into the wall of a tube 3 being inspected (see FIG. 4A). The resulting radially directed beam is particularly useful in detecting cracks or fissures oriented along the longitudinal axis of the tube 3. By contrast, the beam-directing reflector 98 of the probe 13 has a concave, cylindrical contour and is mounted beside the axis of rotation of the probe carrier 7 in order to focus a line-line beam of ultrasound in a chordal direction with respect to the circular cross section of the tube 3 being inspected (see FIG. 4B). The axially offset positioning of the beam-directing reflector 98 of the probe 13 creates a shear wave of ultrasound which is disposed at a 45° angle with respect to the circumference of the tube 3. Such a shear wave of ultrasound is particularly useful in indicated variations in tube wall thickness. Finally, the beam-directing reflector 100 of the probe 15 has a concave, spherical contour which is tilted as shown to focus a point-like beam of ultrasound which is oriented approximately 45° with respect to the axis of the tube 3 (see FIG. 4C). Like the beam-directing reflector 96 of probe 11, the reflector 100 of probe 15 is disposed over the axis of rotation of the probe carrier 7. The resulting axial oriented beam of ultrasound is useful in detecting radially oriented cracks or flaws in the tube walls.

Both the radial beam- and axial beam-directing probes 11 and 15 are approximately 0.25 inches in diameter, while the chordal beam-directing probe 13 is approximately 0.25 inches square. For optimum resolution of tube flaws, the radial beam-directing probe 11 is operated at approximately 20 mHz, while the chordal beam-directing probe 13 and axial beam-directing probe 15 are each operated at approximately 10 mHz. Moreover, the focal depth of each of the beams produced by the probes 11, 13 and 15 is preferably approximately 0.05 inches deep in the wall of an Inconel® 600 tube having an inner diameter of 0.775 inches when the probe carrier 7 is centered within the tube 3. Each of the probes 11, 13 and 15 is ultimately connected to its respective ultrasonic pulser-receiver 54, 56 and 58 via lead wires 102, 104 and 106 preferably embedded in the dielectric material forming the semi-cylindrical center portion of the probe carrier 7. From thence, each of these lead wires extends through the hollow interior of the previously mentioned nipple member 92, and into the inlet of a cable connector 108 where they are electrically connected to a cable 110 coiled in spiral form throughout the interior of the cable housing 9. Such a coiled configuration of the cable 110 allows it to easily extend and retract to accommodate the helical movement of the probe carrier 7 with respect to the drive train housing 8 in much the same fashion as a conventional telephone handset cable.

Turning now to the centering discs 36a, 36b and 38a, 38b that flank the probe carrier 7, each of these disks is connected to a bearing 113, 111, respectively for minimizing angular drag between these discs and the interior walls of the tube being inspected. The proximal bearing 113 is received within a recess 114 in the nipple member 92, while the bearing 111 circumscribes a stub shaft 112. To both facilitate the insertion of the inspection apparatus 1 into a tube and to minimize axial drag as the probe carrier is extended or retracted, each of the centering disks 36a, 36b and 38a, 38b is preferably formed from a resilient, self lubricating plastic material such as nylon.

Turning next to the manner in which the probe carrier 7 is mechanically coupled to the cable housing 9, the cable connector 108 is disposed within a bore 115 of a cylindrical fitting 116 having threads 117 which circumscribe its exterior. A coupling sleeve 118 secures the proximal end of the nipple member 92 to the distal end of the fitting 116 as shown. To this end, the coupling sleeve 118 has, at its proximal end, threads 119 which are engageable with the threads 117 of the fitting, as well as an annular flange 121 on its distal end for engaging a retaining flange 123 which circumscribes the proximal end of the nipple member 92. The distal end of the cable connector 108 is in turn screwed into the proximal end of the nipple member 92 by way of threads 125. To complete the coupling, the exterior threads 117 of the fitting 116 are engaged to the interior threads 127 located at the distal end of the cable housing 9.

Cable housing 9 is generally formed from a cylindrical body 128 having a tapered interior 129 for housing the previously mentioned spiral coiled cable 110. At its distal end, the cylindrical body 128 of the housing 9 is integrally formed with the previously mentioned drive sleeve 32. The drive sleeve 32 is received within the interior of the stationary drive train housing 8, and is both axially and rotatably movable therein. An annular centering collar 131 fits into recess 133 provided around the distal end of the drive train housing 8 in order to help guide the drive sleeve 32 and the cylindrical body 128 of the cable housing 9 that is integrally connected thereto as the sleeve 32 is axially and rotatably driven. In order to generate the previously mentioned screwwise movement of the drive sleeve 32 with respect to the stationary drive train housing 8, the drive sleeve 32 includes on its proximal end an enlarged threaded shoulder 135 as shown. The threads of the shoulder 135 engage the internal threads 137 disposed around the interior of the distal end of the drive train housing 8. The interior of the enlarged threaded shoulder 135 includes a hexagonal bore 139 which slidably receives the hexagonal exterior of the previously mentioned drive shaft 30 of the helical drive train 20. The slidable engagement between the bore 139 and shaft 30 is important, since it allows the drive sleeve 32 to move axially when rotated by the shaft 30. It should be noted that the shaft 30 advantageously has a hollow interior 141 for housing the proximal end of the cable 110, which helps to minimize the overall width of the inspection apparatus 1, thereby resulting in an apparatus which is particularly well adapted for the inspection of small diameter tubes 3.

A shaft coupling 144 connects the output shaft 146 of the slip ring 128 to the proximal end of the hexagonal shaft 30. A key 148 held in place by an O-ring 150 ensures that rotary motion transmitted by the output shaft 156 of the slip ring 28 will be conducted to the coupling 144. The output of the coupling 144 is centered within the drive train housing by means of a ball bearing 152. Finally, the distal end of the coupling 144 is surrounded by a fluid seal formed from an elastomeric material whose flanges are held in sealing engagement by means of an expander ring 156. The fluid seal 154 prevents the water which must surround the probe carrier 7 in order for the ultrasonic probes 11, 13 and 15 to function from leaking into the drive train housing 8 and thereby shorting out the cable connections contained within the slip ring 28.

The various lead wires 88, 102, 104 and 106 which form the lead cable 110 extend through a concentrically located bore in the bearing 144 and on through an opening in the slip ring 28 (not shown). These leads are in turn connected to various connector rings 158 contained within the interior of the slip ring 28. These connector rings 158 slidably and conductively engage connector pads 160 mounted around the inside of the casing of the slip ring 28. In the preferred embodiment, slip ring 28 is a Model No. CAY-944-18-1 Issue B type ring manufactured by the Airflyte Electronics Corp. located in Bayonne, New Jersey. The input shaft 162 of the slip ring 28 is connected to the output shaft 164 of the encoder 24 by means of the previously mentioned shaft coupling 26b. In the preferred embodiment, optical encoder 24 is a Model No. 012H3 125P/R encoder, manufactured by the MicroMo Corp. located in St. Petersburg, Fla. The input shaft 166 of the encoder 24 is in turn connected to the output shaft 167 of the previously mentioned gearbox 23 by means of the shaft coupling 26a. The motor 22 and gearbox 23 are preferably a Model No. 1219E012G cartridge-type electric motor and a Model No. 12/3 529:1 gearbox, both of which are manufactured by MicroMo Corporation located in St. Petersburg, Florida. For ease in assembly, the motor 22, gearbox 23, and encoder 24 are all mounted within a weldment 170 which is slidably insertable through the proximal end of the drive train housing 8. At its proximal end, the drive train housing 8 further includes a threaded base member 172. A pair of O-rings 174a, 174b prevent water or other conductive liquids from penetrating the fit between the exterior end of the base member 172, and the inner walls of the drive train housing 8. Disposed within the threaded base member 172 is a connector assembly 176 having a plurality of pins for receiving a socket (not shown) for the previously mentioned cables 40 and 46.

The method of the invention is reflected in the flow chart illustrated in FIG. 5.

After the inspection apparatus has been slidably inserted into a particular heat exchanger tube 3 so that the probe carrier 7 is adjacent to the region of the tube 3 that the operator wishes to inspect, the operator first selects the precise axial length of the tube 3 he wishes to scan, as is indicated by the box 180. Next, the computer 44 converts this axial length into numbers of scans, as is indicated by box 181. This is a simple operation, which is determined on the basis of the pitch of the screw thread within the proximal end of the housing assembly 6. In the preferred embodiment, the pitch of this screw thread is approximately 0.035 inches, which is small enough to provide a fine resolution scan of a heat exchanger tube 3 in as small a time period as possible.

After the computer 44 has determined the number of scans corresponding to the selected axial length of tube 3 to be inspected, the system operator selects the angular increment of data acquisition, as is indicated by box 182. If the operator desires a relatively quick, coarse resolution scan of the tube 3, this angular increment may be as high as 15°. If, on the other hand, he wishes to have a fine resolution but relatively slower scan made of the axial length being inspected, this angular increment may be as low as 1°. Normally, to provide for a uniform resolution throughout the entire 360° of the scan, the angular increment inspected in step 182 will be a number of degrees which is evenly divisible into 360°.

In the next step 184 of the method of the invention, the electric motor 22 of the helical drive train 20 is actuated so that the output of the encoder is fed into the input of the computer 44, as is indicated by box 185.

Once the computer 44 begins to receive an output from the encoder 185, it inquires whether or not the encoder 24 sweeps past the zero degree position within a selected time period, as is indicated by question block 186. If it does not receive such a signal, it displays an error condition, as is indicated by block 188, which informs the operator of the inspection apparatus that the motor is not properly powering the drive train 20. If, on the other hand, it receives a signal that indicates that the encoder 24 has swept past its zero degree position within the selected time period, it actuates both the ultrasonic and eddy current probes 11, 13, 15 and 17 as soon as it receives the zero degree signal, as is indicated by block 190.

In the next step 192 of this method, the computer 44 commences to record data from all of the probes at the selected angular increment. It converts this data from an analog to a digital signal, and further correlates the datapoints for each probe with the axial and radial position of the probe with respect to the tube 3, as is indicated by the blocks 194 and 195.

Next, the computer 44 enters the digitalized datapoints into its buffer memory along with their correlated axial and radial coordinates within the tube 3 as is indicated in block 196.

In order to determine whether the angular speed of the motor shaft has been set too fast for the particular angular data acquisition increment selected in block 182, the computer 44 monitors whether or not data is being registered for each angular increment, as is indicated by inquiry block 198. If the answer to this question is No, the computer 44 displays an error signal to the operator, as is indicated by block 200. However, if the answer to this inquiry is Yes, the computer 44 proceeds to inquiry block 202, where it asks whether or not the selected number of scans has occurred. If the answer to this question is No, the computer 44 loops back to box 194 as indicated. But if the answer to this inquiry is Yes, the computer proceeds to block 204, where data acquisition is stopped.

Because of the axial distances between the ultrasonic and eddy current probes 11, 13, 15 and 17, much of the data cannot be displayed on the CRT screen 74 in real-time. Accordingly, the operator of the apparatus 1 will normally wait until the number of scans has been completed before displaying this data. However, when the data is displayed, the data acquired by the three ultrasonic probes 11, 13 and 15 is displayed along a Y axis on the right-hand side of the screen for each axial and radial (or Z and X axis) position on the inner walls of the tube 3, while the data acquired by the eddy current probe 17 is displayed on the left-hand side of the screen for each axial and radial (or Z and X axis) position on the inner walls of the tube 3. The end result is that two three-dimensional families of curves represented as surfaces in three-space are displayed across from one another on the left- and right-hand portions of the CRT screen 74, respectively. As has been mentioned earlier, the simultaneous display of data acquired from radial beam, chordal beam, and axial beam ultrasonic probes, in combination with the data acquired by a pancake-type eddy current probe, displays flaw-detecting information which is complementary in nature for each set of cylindrical coordinates on the inner walls of the tube 3, and hence is much more informative and accurate than data acquired by either ultrasonic probes or eddy current probes alone.

We claim:

1. An apparatus for inspecting the walls of an elongated conduit having a circular cross section with both ultrasound and eddy currents, comprising:
   (a) a housing assembly insertable within a elected conduit,
   (b) a probe carrier rotatably connected to and helically movable with respect to said housing, including at least three ultrasonic probes for transmitting ultrasonic beams that are directly oriented radially, chordally and axially with respect to the circular cross section of the conduit, and an eddy current probe (for simultaneously generating eddy currents in the walls of the conduit when the probe carrier is rotated, and
   (c) a helical drive train for helically moving the probe carrier with respect to the housing assembly whereby said conduit walls are helically scanned both ultrasoncially and electromagnetically.

2. The apparatus of claim 1, wherein said helical drive train includes a lead screw assembly for axially moving the probe carrier with respect to the housing assembly when the probe carrier is rotated.

3. The apparatus of claim 1, wherein said helical drive train includes a motor-means for rotating the probe carrier with respect to the housing assembly, and an optical encoder means coupled to the output of the motor means.

4. The apparatus of claim 1, wherein the probe carrier includes a mounting surface that is substantially co-planar with its axis of rotation, and wherein each of the three ultrasonic probes includes a beam directing reflector mounted on said mounting surface.

5. The apparatus of claim 1, wherein the radial and axial beam directing probes are mounted substantially in alignment with the axis of rotation of the probe carrier while the chordal beam directing probe is mounted to one side of said axis.

6. The apparatus of claim 1, wherein the ultrasonic probes are connected to pulser-receiver means by way of an electrically conductive slip ring.

7. The apparatus of claim 1, wherein the probe carrier includes at least one cylindrical shoulder and wherein said eddy current probe is mounted in the shoulder.

8. The apparatus of claim 7, wherein said eddy current probe is resiliently mounted on the outer surface of the cylindrical shoulder so as to resiliently engage the inner surface of the conduit wall when said probe carrier is helically moved.

9. An apparatus for ultransonically and electromagnetically inspecting the walls of an elongated tube having a circular cross section, comprising:
   (a) a housing assembly insertable with a tube;
   (B) a probe carrier rotatably mounted on and helically movable with respect to said housing assembly, including three ultrasonic probes for transmitting ultrasonic beams that are directly oriented radially, chordally and axially with respect to the circular cross section of the tube and an eddy current probe for simultaneously transmitting electromagnetic lines of flux through the walls of the tube when the probe carrier is rotated and
   (c) a helical drive train for helically moving the probe carrier with respect to the housing assembly.

10. The apparatus of claim 9, wherein said helical drive train includes a motor means for rotating the probe carrier within said housing assembly, and a lead screw assembly for axially moving the probe carrier when it is rotated.

11. The apparatus of claim 10, wherein the helical drive train further includes an optical encoder means for indicating the relative amount of rotational movement between the probe carrier and the housing assembly.

12. The apparatus of claim 11, wherein said lead screw assembly includes a drive shaft for coupling the output of the motor means with the probe carrier, said shaft having a bore along its longitudinal axis for receiving wires which connect the ultrasonic probes to pulser-receiver means.

13. The apparatus of claim 12, wherein the rotary output of the motor means, the optical encoder means and the axis of the shaft are arranged substantially along the axis of rotation of the probe carrier in order to minimize the width of the apparatus.

14. The apparatus of claim 10, wherein the lead screw assembly includes a shaft, and a drive sleeve whose interior is slidably engaged to and axially movable along said shaft, and whose exterior is threaded.

15. The apparatus of claim 14, wherein the housing assembly further includes a drive train housing whose interior includes threads that are engaged to the threaded exterior of the drive sleeve.

16. The apparatus of claim 9, wherein said probe carrier is formed from a lightweight, dielectric material.

17. The apparatus of claim 9, wherein the outputs of the ultrasonic probes and eddy current probe are electrically connected to the input of a computer means.

18. The apparatus of claim 11, further including a computer means, wherein the output of the optical encoder means is connected to the input of the computer means, and the output of the computer means controls the motor means 19. An apparatus for inspecting the walls of an elongated tube having a circular cross section with both ultrasound and eddy currents, comprising:
   (a) a housing assembly insertable within a selected tube;
   (b) a probe carrier rotatably mounted on and helically movable with respect to said housing assembly, including three ultrasonic probes for transmitting separate ultrasonic beams that are directly oriented radially, chordally and axially with respect to the circular cross section of the tube, and an eddy current probe for simultaneously generating eddy currents in the walls of the tube when the probe carrier is rotated;
   (c) a helical drive train for helically moving the probe carrier with respect to the housing assembly, including a motor means connected to a source of electrical power for rotating the probe carrier, an optical encoder means for indicating the relative amount of rotational movement between the probe carrier and the housing assembly, and a lead screw assembly for axially moving the probe carrier when it is rotated, and
   (d) a computer means whose input is electrically connected to the optical encoder means, and to the outputs of the three ultrasonic probes and the eddy current probe, and whose output is connected to the source of electrical power in order to regulate the amount of power transmitted to the motor means.

20. The apparatus of claim 19, wherein each of the three ultrasonic probes includes a separate, beam directing means.

21. The apparatus of claim 20, wherein the probe carrier includes a mounting surface that is substantially co-planar with the axis of rotation of the probe carrier.

22. The apparatus of claim 21, wherein the radial and axial beam directing probes are mounted substantially in alignment with the axis of rotation of the probe carrier while the chordal beam directing probe is mounted to one side of said axis.

23. The apparatus of claim 19, wherein the lead screw assembly includes a shaft, and a drive sleeve whose interior is slidably engaged to and axially movable along said shaft, and whose exterior is threaded.

24. The apparatus of claim 23, wherein the housing assembly further includes a drive train housing whose interior includes threads that are engaged to the threaded exterior of the drive sleeve.

25. The apparatus of claim 23, wherein said shaft includes a bore for housing wires that connect the three ultrasonic probes and the eddy current probe to sources of power.

26. The apparatus of claim 19, wherein said lead screw assembly includes a shaft for coupling the output of the motor means with the probe carrier, said shaft having a bore along its longitudinal axis for receiving wires which connect the ultrasonic probes to pulser-receiver means.

27. An apparatus for inspecting the walls of a metallic heat exchanger tube having a circular cross section simultaneously with ultrasonic probes and an eddy current probe, comprising:
  (a) a cylindrical housing assembly insertable within said tube;
  (b) a probe carrier rotatably mounted on and helically movable with respect to said housing assembly, including three ultrasonic probes for transmitting separate ultrasonic beams that are respectively oriented substantially radially, chordally and axially with respect to the circular cross section of the tube, and a pancake-type eddy current probe for scanning the tube walls with lines of electromagnetic flux when the probe carrier is rotated and helically moved, and
  (c) a helical drive assembly including a motor means, and a lead screw assembly having an elongated shaft that is coupled to the output of the motor means, and a threaded drive sleeve that is rotatably connected to said shaft but is slidably movable along the longitudinal axis thereof, wherein said drive sleeve is further connected to said probe carrier in order to move said carrier along a helical path with respect to said housing assembly.

28. A method of inspecting the walls of a tube having a circular cross section with both beam-type ultrasonic probes and an eddy current probe, characterized by the steps of:
  (a) orienting the ultrasonic beams of three separate ultrasonic probes radially, chordally and axially with respect to the cross section of the tube;
  (b) orienting an eddy current probe so that the lines of electromagnetic flux emanated thereby intersect with a section of the tube wall exposed to one or more of the beams transmitted by the ultrasonic probes; and
  (c) helically moving the three ultrasonic probes and one eddy current probe within the tube in order to simultaneously scan the walls of the tube with ultrasound and electromagnetic flux.

29. The method of claim 28, further including the step of storing the data generated by each of the probes.

30. The method of claim 29, further including the step of correlating the data generated by each probe with a specific radial and axial tube position.

31. The method of claim 29, further including the step of simultaneously displaying the data generated by each probe for a specific angular and axial position in the tube.

* * * * *